United States Patent
Popescu et al.

(10) Patent No.: US 7,646,843 B2
(45) Date of Patent: Jan. 12, 2010

(54) METHOD FOR PRODUCING PROJECTIVE AND TOMOGRAPHIC PHASE CONTRAST IMAGES WITH THE AID OF AN X-RAY SYSTEM

(75) Inventors: Stefan Popescu, Erlangen (DE); Björn Heismann, Erlangen (DE); Eckhard Hempel, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 246 days.

(21) Appl. No.: 11/700,032

(22) Filed: Jan. 31, 2007

(65) Prior Publication Data

US 2007/0183560 A1    Aug. 9, 2007

(30) Foreign Application Priority Data

Feb. 1, 2006  (DE) ..................... 10 2006 004 976
Apr. 3, 2006  (DE) ..................... 10 2006 015 356

(51) Int. Cl.
   *G01N 23/083*   (2006.01)
   *G01B 9/02*     (2006.01)
(52) U.S. Cl. ................. 378/5; 378/9; 378/85; 356/521
(58) Field of Classification Search ............... 378/4, 378/5, 9, 15, 16, 19, 82, 85; 356/305, 328, 356/517, 518, 521; 250/201.9, 550, 234–236, 250/237 R, 237 G
See application file for complete search history.

(56) References Cited

U.S. PATENT DOCUMENTS

| | | | | |
|---|---|---|---|---|
| 4,562,540 A | * | 12/1985 | Devaney ................. | 700/90 |
| 5,684,851 A | * | 11/1997 | Kurbatov et al. .......... | 378/87 |
| 5,812,629 A | * | 9/1998 | Clauser ................. | 378/62 |
| 2004/0062452 A1 | | 4/2004 | Sakaida | |
| 2004/0174959 A1 | | 9/2004 | Green | |
| 2005/0220265 A1 | | 10/2005 | Besson | |
| 2005/0286680 A1 | * | 12/2005 | Momose ................. | 378/62 |

OTHER PUBLICATIONS

Weitkamp, Timm et al.: "X-ray phase imaging with a grating interferometer", Optics Express, vol. 13, No. 16, published Aug. 8, 2005, pp. 6296-6304.

V.N. Ingal, E.A. Beliaevskaya: "X-ray plane-wave topography observation of the phase contrast from a non-crystalline object", X-Ray Laboratory, Russia, J.Phys.D.: Appl.Phys., vol. 28, 1995, pp. 2314-2317.

Bonse, U., Hart M.: "An X-ray interferometer", Applied Physics Letters, vol. 6, No. 8, Apr. 15, 1965, pp. 155-156.

(Continued)

*Primary Examiner*—Allen C. Ho
*Assistant Examiner*—Anastasia Midkiff
(74) *Attorney, Agent, or Firm*—Harness, Dickey & Pierce, P.L.C.

(57) ABSTRACT

A method is disclosed for producing projective and tomographic phase contrast images of an examination object, preferably a patient, with the aid of an X-ray system, and a corresponding X-ray system for carrying out this method. In at least one embodiment of the method, X-ray optical grating sets tuned to different energy ranges are used to determine energy-dependent phase shifts upon penetration of an examination object, a difference value is formed from these energy-dependent phase shifts, and tomographic or projective images are produced therefrom.

49 Claims, 5 Drawing Sheets

OTHER PUBLICATIONS

Mayo, S-C., et al.: Quantitative X-ray projection microscopy: phase-contrast and multi-spectral imaging. In: Journal of Microscopy, 2002, vol. 207, S. 79-96.

Weitkamp, T. et al: X-ray phase imaginn with a grating interferometer. In: Optics Express, 2005, vol. 13, No. 16, S. 6296-6304.

Pfeiffer, F. Weitkamp et al.: Phase retrieval and differential phase-contrast imaging with low-brilliance X-ray sources. In: Nature Physics, 2006, vol. 2, S. 258-261.

Senoussaoui, N.: Thin film solar cells with periodic grating coupler. In: Thin Solid Films, 2004, vol. 451-452, S. 397-401.

German Office Action.

* cited by examiner

METHOD FOR PRODUCING PROJECTIVE AND TOMOGRAPHIC PHASE CONTRAST IMAGES WITH THE AID OF AN X-RAY SYSTEM

PRIORITY STATEMENT

The present application hereby claims priority under 35 U.S.C. §119 on German patent application numbers DE 10 2006 004 976.4 filed Feb. 1, 2006, and DE 10 2006 015 356.1 filed Apr. 3, 2006, the entire contents of each of which is hereby incorporated herein by reference.

FIELD

Embodiments of the invention generally relate to methods for producing projective and tomographic phase contrast images of an examination object, preferably a patient, with the aid of an X-ray system; moreover, embodiments of the invention also generally relate to corresponding X-ray systems for carrying out this method.

BACKGROUND

In general computer tomography, tomographic images of an examination object, in particular of a patient, are taken with the aid of absorption measurements of X-rays that penetrate the examination object, a radiation source generally being moved in the shape of a circle or spiral about the examination object, and a detector, for the most part a multi-row detector with a multiplicity of detector elements, measuring the absorption of the radiation upon passage through the examination object on the side opposite the radiation source. For the purpose of tomographic imaging, tomographic slice images or volume data are reconstructed from the measured absorption data of all the measured spatial rays. Very fine absorption differences in objects can be displayed with the aid of these computer tomography images, but zones of similar chemical composition that naturally also have a similar absorption behavior are displayed only with unsatisfactory detail.

It is known, furthermore, that the effect of the phase shift upon passage of a beam through an examination object is substantially stronger than the absorption effect of the material penetrated by the radiation. Such phase shifts are known to be measured by the use of two interferometric gratings. These interferometric measuring methods are referred to, for example, in "X-ray phase imaging with a grating interferometer, T. Weitkamp et al., Aug. 8, 2005/Vol. 12, No. 16/OPTICS EXPRESS".

In the case of this method, an examination object is irradiated by a coherent X-radiation and subsequently guided through a pair of gratings, and the radiant intensity is measured directly after the second grating. The first grating produces an interference pattern that images a moiré pattern on to the detector lying therebehind with the aid of the second grating. If the second grating is slightly displaced, this likewise results in a displacement of the moiré pattern, that is to say a change in the spatial intensity in the detector lying therebehind, which can be determined relative to the displacement of the second grating. If the change in intensity is plotted for each detector element of this grating that is to say for each beam, as a function of the displacement path of the second grating, the phase shift of the respective beam can be determined. The fact that this method requires a very small radiation source is a problem, and therefore cannot be applied in practising computer tomography of relatively large objects, since formation of the interference pattern requires a coherent radiation.

In one possibility, the method shown in the abovenamed document requires a radiation source with an extremely small focus such that a sufficient degree of spatial coherence is present in the radiation used. However, when such a small focus is used there is then, in turn, an insufficient dose rate for examining a relatively large object. However, there is also the possibility of using a monochromatically coherent radiation, for example, a synchrotron radiation, as radiation source, but the construction of the CT system is thereby rendered very expensive and so a widespread application is impossible.

This problem can be circumvented by arranging a first absorption grating inside the focus/detector combination in the beam path, directly following the focus. The alignment of the grating lines is in this case parallel to the grating lines of the interference grating following the examination object.

The slits of the first grating produce a field of individually coherent beams that suffices for producing the interference pattern known per se with the aid of the phase grating arranged downstream of the object in the beam direction.

It is possible in this way to use radiation sources that have dimensions corresponding to the normal X-ray tubes in CT systems or transmitted light X-ray systems such that, for example, it is now also possible to make well differentiated soft part images in the field of general medical diagnostics with the aid of X-ray machines.

However, it has emerged that, despite this described improvement, it would be advantageous to obtain a further improved differentiation of the structure of an examination object, in particular of the soft structure of a patient.

SUMMARY

In at least one embodiment of the invention, the method of phase contrast imaging in terms both of method and apparatus is improved to the effect that the recorded results enable a stronger differentiation of structures of similar chemical makeup.

The inventors, in at least one embodiment, have realized that it is possible to improve the differentiation of structures of similar chemical makeup by measuring the phase shift of X-ray beams on penetration of an object as a function of different X-ray energies, by subsequently preparing differentiating functions for differentiating the scanned tissue from the measured phase shifts. Thus, the simplest possible way is to form the difference between the phase shifts measured with different energies: a quotient can be formed from the two energy-dependent, measured phase shifts, or for each measured pixel or voxel of a projective or tomographic image a type of normalized contrast index such as is described later can be determined from these values. Instead of the phase shift itself, it is also possible to use the absorption index n, which is linearly related to the phase shift, and to form corresponding typical differentiation values.

If this basic method is applied, for example, to a computer tomography image, it is already possible to form these differentiation values before the actual reconstruction such that the projections that are later reconstructed therefore already comprise the differentiation values. However, it is also possible to use the phase shifts and/or refractive indices for the reconstruction of energy-dependent tomographic images and, once the reconstruction is done, to take the individual image voxels or pixels from sectional images of the same location in each case, and not until then to form the differentiation values therefrom.

In accordance with the basic idea of at least one embodiment of the invention, the inventors therefore propose, on the one hand, a method for producing projective images, that is to say transmitted-light X-ray images, on the basis of phase contrast measurements, while on the other hand a method is also proposed for producing tomographic images with the aid of at least two phase contrast measurements with the use of different energy ranges. The inventors, in at least one embodiment, likewise propose corresponding X-ray systems for producing the abovenamed projective images, and also X-ray computer tomography systems for producing such images on the basis of tomographic reconstructions.

It follows according to at least one embodiment of the invention that the proposed method for producing projective or tomographic images of an examination object, preferably a patient, with the aid of an X-ray system by using spatial recorded values together with a measurement of phase shifts of an X-radiation penetrating the examination object comprises measuring the phase shift in an energy-specific fashion with reference to at least two different energy ranges, and forming recorded values as a function of the energy-specific phase shift.

This renders it possible for even small differences in the chemical makeup of the examined object to be detected with the aid of a particularly sensitive "probe". The selectivity of at least one embodiment of this method is particularly acute when the energy ranges of the X-radiation that are used reach beyond the absorption edges known per se with reference to the material examined or tissue examined, that is to say when the at least two energy ranges of the X-radiation that are used lie on both sides of an edge with reference to the energy-specific refractive index of the material examined.

Although at least one embodiment of the method is thus also suitable in principle for measuring a multiplicity of different energy ranges, the chief proposal is, nevertheless, to determine exactly two energy-specific phase shifts for exactly two energy ranges.

The value $$\frac{\varphi(E1) - \varphi(E2)}{\varphi(E1) + \varphi(E2)}$$

can preferably be used as a function of the energy-specific phase shifts, the variable $\phi(E_x)$ standing for a measured phase shift in the energy range $E_x$.

Alternatively, the quotient $$\frac{\varphi(E1)}{\varphi(E2)}$$

or a difference value $\phi(E1)-\phi(E2)$ can also be used for example.

As already previously mentioned, it is also possible to calculate in each case the energy-specific refractive index from the measured energy-specific phase shifts, and to use these values for the recorded values. The conversion of the energy-specific refractive indices can be determined in accordance with the relationship $$\varphi = 2\pi n \frac{v}{\lambda}$$

$\lambda$ represents the wavelength of the X-radiation of the energy range considered, and v represents the extent of a voxel.

It may be pointed out in this context that the talk within the scope of embodiments of this invention is mostly not of a specific energy, but a specific energy range since, of course, it is not the case that the given method of measurement determines the phase shift with reference to an energy of pinpoint accuracy, but that what is involved here in practice is actually energy ranges, that is to say an energy interval.

In accordance with the abovedescribed functions for the energy-specific phase shifts, it is also possible to use corresponding functions for the energy-specific refractive indices, preferably via the function $$\frac{n(E1) - n(E2)}{n(E1) + n(E2)}$$

or the quotient $$\frac{n(E1)}{n(E2)}$$

or simply the $\Delta$-value $n(E1)-n(E2)$.

With reference to the use of at least one embodiment of this method for producing the tomographic X-ray phase contrast images, it is further proposed to carry out at least the following method steps:

the examination object is scanned with at least one focus/detector system in a circular or spiral fashion, the detector system having a multiplicity of juxtaposed detector elements that form at least one detector row, preferably a number of detector rows, arranged between the at least one focus and the at least one detector for the purpose of measurement is a set of X-ray optical gratings that is transirradiated by the X-radiation, a field of radiation sources with individually coherent radiation being generated with the aid of at least one source grating between the focus and examination object, the examination object being penetrated by the X-radiation, and the X-radiation being subjected to a different phase shift depending on the penetrated matter, an interference pattern of the radiation of this energy range being generated with the aid of a first phase grating tuned to a first energy range (E1), at least one further interference pattern of radiation of this energy range being generated with the aid of at least one second phase grating tuned to another energy range (E2), the radiation being guided to the detector through an analyzer grating, and the phase shift of each beam upon passage through the examination object being determined by means of at least three intensity measurements of the same spatial beam with in each case a differently offset analyzer grating, and tomographic phase contrast data of the examination object are reconstructed from the measured phase shifts of the beams or refractive indices determined therefrom.

A dedicated focus/detector system respectively having a grating set adapted in an energy-specific fashion can be used for the measurements of the phase shifts wherein per energy range, the focus/detector systems advantageously can be arranged with an angular offset on a gantry.

However, there is also the possibility of making use for each energy range solely of different phase gratings in the same focus/detector system for the measurements of the phase shifts. To this end, either it is possible for the different phase gratings at different distances from the focus to be set manually, or an apparatus can be provided, by which they can be displaced laterally in the direction of the system axis or else in a circumferential direction.

It is proposed, furthermore, that the energy of a peak in the characteristic radiation of the anode material employed is used for at least one energy range to which at least one analyzer grating is tuned. For example, this can involve the $K_\alpha$ line and the $K_\beta$ line of the anode material, preferably tungsten as anode material.

However, there is also the possibility of generating the X-radiation for at least two different energy ranges with the aid of different anode materials.

If consideration is given to the method for producing projective phase contrast images, that is to say phase contrast images in the case of which in order to form a projection image use is made not of reconstruction methods, but solely of the phase shifts measured during the transirradiation of the examination object, the inventors, in at least one embodiment, particularly propose the application of the following features:

the examination object is transirradiated by a beam emanating from the focus of an X-ray tube, the received radiation intensity is measured with a detector, there being arranged between the at least one X-ray tube and the detector a set of X-ray opticagratings comprising at least one source grating, at least two different phase gratings alternately introduced into the beam path, and an analyzer grating, for each beam that lies in space between the focus and detector and penetrates the examination object, the phase shift of this beam upon penetrating the object is determined by at least three intensity measurements with the aid of an analyzer grating arranged in each case with a different offset, and for each beam the pixel values are calculated as a function of the energy-specific phase shifts ($\phi(E1)$, $\phi(E2)$) from the measured phase shifts for different energy ranges ($\phi(E1)$, $\phi(E2)$) of each beam.

It is also proposed here to make use for at least one energy range in which the at least one analyzer grating is tuned of the energy of a peak in the characteristic radiation of the anode material employed. For example, it is also possible here to employ the $K_\alpha$ line and $K_\beta$ line of the anode material, preferably made from tungsten, as anode material. Likewise, the X-radiation for at least two different energy ranges can be generated with the aid of different anode materials. It may be pointed out in this context that it is not mandatory to use different X-ray tubes in order to work with different anode materials. For example, it is possible to design an anode, in particular a rotary anode, such that there is a jump focus that respectively jumps to different regions of the anode that are occupied by different materials. Alternatively, it is also possible to use a rotary anode that is occupied in segments by different anode materials such that, for example, the anode material respectively desired for generating the X-radiation is used by means of an appropriate time control of the tube current.

The inventors also propose, in accordance with at least one embodiment of the method outlined above, at least one embodiment of an X-ray CT system for producing tomographic phase contrast images that has at least one focus/detector system arranged on a gantry or a C arc such that it can rotate about an examination object, and a set of transirradiated X-ray optical gratings between the focus and detector, comprising at least one source grating, at least two phase gratings that can be alternately moved into the beam path, and an analyzer grating.

As an alternative thereto, there is also proposed an X-ray CT system that has at least two focus/detector systems arranged on a gantry or a C arc such that they can rotate about an examination object, and for each focus/detector system, a set of transirradiated X-ray optical gratings, dimensioned in an energy-specific fashion, between the focus and detector, comprising a source grating, a phase grating and an analyzer grating.

It is to be noted in this case that the two abovenamed variants can also be combined such that, for example, two focus/detector systems arranged with an angular offset on a gantry are respectively equipped with two or more different grating sets, and there is thus a greater degree of variability in the selection of the examined energy ranges used for measuring the phase shift.

These inventive CT systems preferably have, in at least one embodiment, an apparatus provided for the relative displacement of the analyzer grating with reference to the phase grating in a fashion perpendicular to the beam direction and perpendicular to the longitudinal direction of the grating lines.

In an additional variant, it can also be provided that at least one further focus/detector system is arranged with an angular offset on the gantry, which is free from X-ray optical gratings and serves exclusively for absorption measurement.

According to at least one embodiment of the invention, it is, moreover, proposed that the grating arrangement of the inventive X-ray CT systems satisfies the following geometric conditions:

for the first grating set:

$$p_{11} = 2 \times \frac{p_{01} \times p_2}{p_{01} + p_2}$$

$$p_{01} = p_2 \times \frac{l_1}{d_1},$$

$$d_1 = \frac{l_1 \times d_1^=}{l_1 - d_1^=} \text{ where } d_1^= = \frac{1}{2} \times \left(\frac{p_1^2}{4\lambda_1}\right),$$

$$h_{11} = \frac{\lambda_1}{2(n-1)},$$

and for the second grating set:

$$p_{12} = 2 \times \frac{p_{02} \times p_2}{p_{02} + p_2}$$

$$p_{02} = p_2 \times \frac{l_2}{d_2},$$

$$d_2 = \frac{l_2 \times d_2^=}{l_2 - d_2^=} \text{ where } d_2^= = \frac{1}{2} \times \left(\frac{p_2^2}{4\lambda_2}\right),$$

-continued $$h_{12} = \frac{\lambda_2}{2(n-1)},$$

where:
$p_x$=Grating period of the grating $G_x$,
$p_{xy}$=Grating period of the grating $G_{xy}$,
$l_x$=Distance of the source grating $G_0$ from the phase grating $G_{1x}$ for the energy range $E_x$,
$d_x$=Distance of the phase grating $G_{1x}$ for the energy range $E_x$ from the analyzer grating $G_2$ in fan beam geometry,
$d_1{}^=$=Distance of the phase grating $G_{1x}$ for the energy range $E_x$ from the analyzer grating $G_2$ given parallel geometry,
$\lambda_x$=Wavelength of the radiation in the energy range $E_x$,
$h_{1x}$=Web height of the grating $G_{1x}$ for the energy range $E_x$ in the radiation direction, and
n=Refractive index of the grating material.

On the basis of the given grating arrangement, the latter can satisfy the geometric condition $l_1+d_1=l_2+d_2$, it then being necessarily the case that the periods of the source gratings used are different, that is to say $p_{01} \neq p_{02}$. Alternatively, the periods of the source gratings used can be selected to be identical, that is to say $p_{01}=p_{02}$, it then being possible for the grating arrangement to satisfy the geometric condition $l_1+d_1 \neq l_2+d_2$. In accordance with a further alternative, it is the case both that the source grating can have a different period, and that the distance between the source grating and analyzer grating can be selected to be different.

Such an X-ray CT system of at least one embodiment can, furthermore, have an arithmetic and control unit that contains the program code that carries out the abovedescribed method during operation.

Moreover, the scope of at least one embodiment of the invention includes a storage medium of a CT system or for a CT system that contains the abovenamed program code.

Furthermore, at least one embodiment of the invention features a focus/detector system of an X-ray apparatus comprising at least:
a radiation source with a focus and an opposing planar detector with a multiplicity of detector elements,
a set of transirradiated X-ray optical gratings of parallel alignment that is arranged between the focus and detector and by means of which the phase shift of the radiation upon penetration of the examination object can be measured in a beamwise resolved fashion, the grating set having:
at least one source grating that is arranged between the at least one focus and the examination object,
at least two phase gratings that can be arranged between the examination object and the detector and be alternately introduced into the beam path,
an analyzer grating that is arranged upstream of the detector, and
an apparatus for the relative displacement of the analyzer grating with reference to the phase gratings in a fashion perpendicular to the beam direction and perpendicular to the longitudinal direction of the grating lines.

The inventors, in at least one embodiment, also correspondingly propose an X-ray system including the previously described focus/detector system, additional device(s), preferably an arithmetic logic unit, being provided for calculating the phase shift from a number of intensity measurements of the same beam with the aid of differently offset phase gratings.

It is also proposed, in at least one embodiment, for such an X-ray system and/or a corresponding focus/detector system that the gratings be arranged in accordance with the above named geometric conditions.

Furthermore, there is also proposed an X-ray system for producing projective images that contains an arithmetic and control unit that contains program code that executes at least one embodiment of the above described method during operation.

At least one embodiment of the invention likewise includes a storage medium of such an X-ray system or for such an X-ray system, which contains corresponding stored program code.

BRIEF DESCRIPTION OF THE DRAWINGS

The invention is described in more detail below with reference to an example embodiment and with the aid of the figures, only the features necessary for understanding the invention being illustrated. The following reference symbols are used in this case: 1: CT system; 2: first X-ray tube; 3: first detector; 4: second X-ray tube; 5: second detector; 6: gantry housing; 7: patient; 8: patient couch; 9: system axis; 10: control and arithmetic unit; 11: memory; 12: schematic of an embodiment of the inventive method; A: path A; B: path B; $D_1, D_2$: detector; $d_1, d_2$: distance between phase grating and analyzer grating; E1: first energy range; E2: second energy range; $E_i$: ith detector element; $F_1, F_2$: focus; $G_0, G_{01}, G_{02}$: source gratings; $G_{11}, G_{12}$: phase gratings; $G_2, G_{21}, G_{22}$: analyzer gratings; $h_0, h_{11}, h_{12}, h_2$: height of the grating webs; $I(E_1(x_G))$: measured intensity at the detector element $E_1$ with a grating offset of $x_G$; $K_\alpha, K_\beta$: characteristic X-ray peaks; $l_1, l_2$: distance between source grating and phase grating; P: patient; $p_{01}, p_{02}, p_{11}, p_{12}, p_2$: period of the grating lines; $Prg_x$: programmes; S: system axis; $x_G$: offset of the analyzer grating; w: extent of the focus; x, y, z: Cartesian coordinates; $u(\phi(E1), \phi(E2))$: difference functions of the phase shift of the voxels of a CT image data record; $\phi$: phase shift; $\phi(Ex)$: phase shift of the radiation of energy Ex; $\lambda$: wavelength of the X-ray radiation considered.

In detail.

DETAILED DESCRIPTION OF THE EXAMPLE EMBODIMENTS

It will be understood that if an element or layer is referred to as being "on", "against", "connected to", or "coupled to"

another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1:
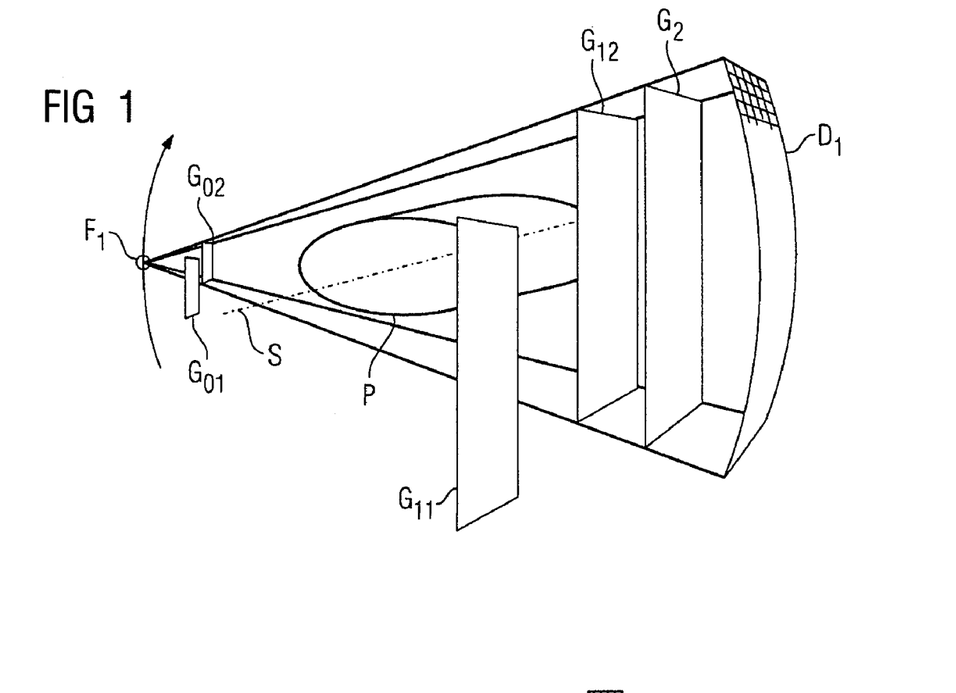
FIG. 1 shows a 3D schematic of a focus/detector system of an X-ray CT.

FIG. 1 shows a 3D schematic of a focus/detector system of an X-ray CT having, as examination object, a patient P lying in the beam path. The focus $F_1$ and the detector $D_1$ are arranged on a gantry (not illustrated in more detail here) and moved in the shape of a circle about the system axis S. If a linear movement of the patient P in the direction of the system axis is additionally carried out during the rotation of the focus/detector system, this results in a spiral scanning, known per se, of the patient P. Three X-ray optical gratings $G_{0x}$, $G_{1x}$, and $G_2$ are arranged in the beam path of the focus/detector system, the first grating $G_{0x}$, which is also termed source grating, being fitted in the immediate vicinity of the focus $F_1$ and being transradiated by the X-radiation.

Following thereafter in the propagation direction of the X-radiation is the actual examination object or the patient P. The second grating $G_{1x}$, termed phase grating, firstly follows upstream of the detector $D_1$ lying on the other side of the system axis S. Following thereafter in the direction of radiation is the third grating $G_2$, termed analyzer grating, that is advantageously arranged immediately upstream of the detector $D_1$.

The detector $D_1$ has at least one row with a multiplicity of detector elements, the detector $D_1$ preferably being designed as a multirow detector that is equipped with a multiplicity of detector rows that are arranged in parallel and each have a multiplicity of detector elements. The connecting lines between the focus $F_1$ and the individual detector elements represent in each case during scanning an X-ray beam that is arranged in space and whose change in intensity is measured by the respective detector element.

It may be pointed out that in the case of so-called C-arc units, which also belong to the class of the CT systems mentioned here, the detector $D_1$ is not, as shown, designed as a cylindrical segment about the focus $F_1$, but has a planar shape. In the case of projective X-ray systems which do not move about the examination object during the scanning, the detector $D_1$ is generally likewise of planar design.

The line orientation of the gratings $G_{0x}$ to $G_2$ is such that the grating lines of all three gratings run parallel to one another and, in addition, are oriented parallel to the system axis S, the gratings $G_{0x}$ to $G_2$ mostly being of planar design and are lined perpendicular to the center line between the focal point and detector midpoint. However, there is also the possibility in principle of adapting the surface of the gratings to the optical path of the light cone such that at each location the gratings are intersected perpendicularly by the beam connection between the focus and the respective detector element, the result being a corresponding curvature of the gratings.

The arrangement described so far can be used only for measuring the phase shift in a specific energy range in which the grating arrangement is oriented. It is therefore possible either to arrange a number of such focus/detector arrangements with an angular offset on a gantry, each individual focus/detector system then being oriented to different energy ranges with reference to their grating arrangements.

Alternatively, however, it is also possible to use a single focus/detector system—as is shown in FIG. 1—and merely to configure the source gratings and phase gratings, here the gratings $G_{01}$, $G_{02}$ and $G_{11}$, $G_{12}$ in an exchangeable fashion, the two gratings having different positions and/or different periods corresponding to the energy to which they are tuned, it being necessary in each case to fulfill the previously described geometric conditions of the grating sets. Such a variant is illustrated in FIG. 1, in which both the second source grating $G_{01}$ and the second grating $G_{11}$ are arranged outside the beam path such that for the purpose of measuring with the second desired energy, the source grating $G_{02}$ and the phase grating $G_{12}$ are taken out of the beam path, and the source grating $G_{01}$ and the phase grating $G_{11}$ are inserted.

Figure 2:
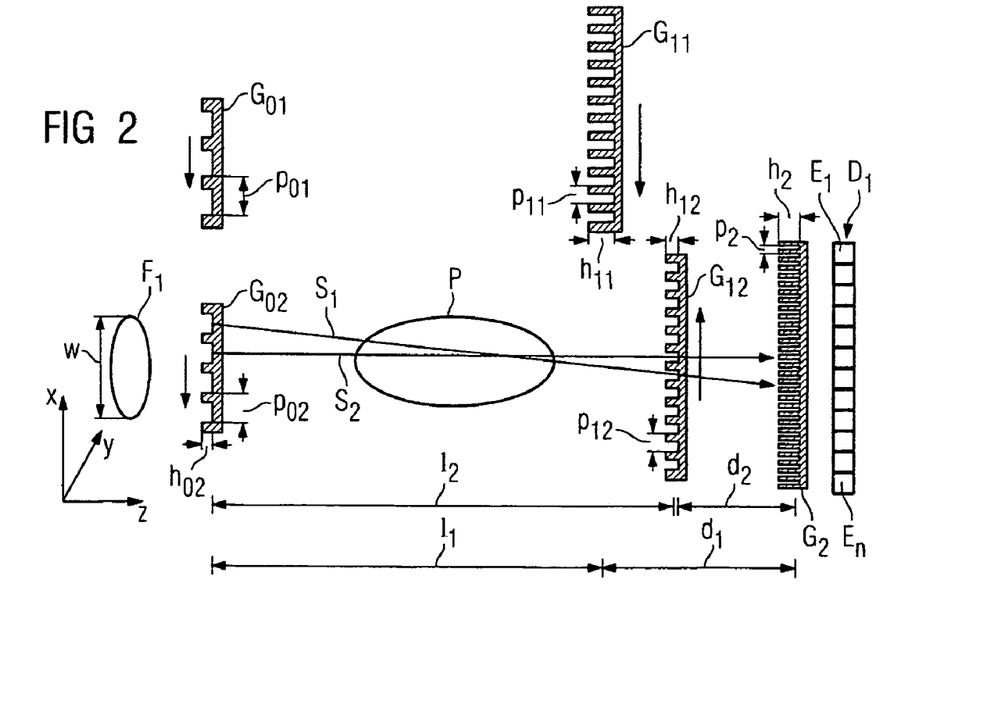
FIG. 2 shows a longitudinal section through a focus/detector system, including an illustration of source gratings, phase gratings and analyzer gratings and their grating structure.

An inventive focus/detector system with two grating sets $G_{01}$, $G_{11}$, $G_2$ and $G_{02}$, $G_{12}$, $G_2$ is illustrated schematically once again in FIG. 2. Located upstream of the first grating $G_{02}$ is the focus $F_1$, whose greatest extent is denoted by w. The first grating $G_{02}$ has a line spacing or grating period $p_{02}$ and a height $h_{02}$ of the grating webs. The gratings $G_{01}$, $G_{12}$ and $G_2$ are correspondingly also equipped with a height $h_{12}$ or $h_2$, and a period $p_{01}$, $p_{11}$ or $p_2$.

It is important for the functioning of the method according to an embodiment of the invention that the distance between the source grating and the phase grating, and the distance between the phase grating and the analyzer grating be at a specific ratio to one another. It holds in this case that:

for the first grating set:

$$p_{11} = 2 \times \frac{p_{01} \times p_2}{p_{01} + p_2}$$

$$p_{01} = p_2 \times \frac{l_1}{d_1},$$

$$d_1 = \frac{l_1 \times d_1^=}{l_1 - d_1^=} \text{ where } d_1^= = \frac{1}{2} \times \left(\frac{p_1^2}{4\lambda_1}\right),$$

$$h_{11} = \frac{\lambda_1}{2(n-1)},$$

and for the second grating set:

$$p_{12} = 2 \times \frac{p_{02} \times p_2}{p_{02} + p_2}$$

$$p_{02} = p_2 \times \frac{l_2}{d_2},$$

$$d_2 = \frac{l_2 \times d_2^=}{l_2 - d_2^=} \text{ where } d_2^= = \frac{1}{2} \times \left(\frac{p_2^2}{4\lambda_2}\right),$$

$$h_{12} = \frac{\lambda_2}{2(n-1)},$$

where:
$p_x$=Grating period of the grating $G_x$,
$p_{xy}$=Grating period of the grating $G_{xy}$,
$l_x$=Distance of the source grating $G_0$ from the phase grating $G_{1x}$ for the energy range $E_x$,
$d_x$=Distance of the phase grating $G_{1x}$ for the energy range $E_x$ from the analyzer grating $G_2$ in fan beam geometry,
$d_1^=$=Distance of the phase grating $G_{1x}$ for the energy range $E_x$ from the analyzer grating $G_2$ given parallel geometry,
$\lambda_x$=Wavelength of the radiation in the energy range $E_x$,
$h_{1x}$=Web height of the grating $G_{1x}$ for the energy range $E_x$ in the radiation direction, and
n=Refractive index of the grating material.

The illustration shows a situation in which the second phase grating $G_{12}$ is currently being used for measurement, and the first phase grating $G_{11}$ is removed from the beam path. In practice, the focus/detector system respectively used would have an apparatus that automatically inserts the phase gratings into the beam path depending on need, or removes the undesired grating. It is also possible here to arrange more than two phase gratings at respectively different distances from the focus in the beam path.

The distance of the detector $D_1$ with its detector elements $E_1$ to $E_n$ from the respective analyzer grating $G_2$ is not critical, but the latter should be arranged as near as possible to the detector.

In one advantageous variant, the phase gratings $G_{11}$ and $G_{12}$ can be set in each case to an energy that corresponds to a characteristic line in the X-ray spectrum of the anode used. With the currently customary tungsten anodes, it is advantageously possible, for example, to use their $K_\alpha$ line and the $K_\beta$ line lying close thereto. When other anode materials are selected, other energies, and thus other dimensions of the phase grating correspondingly become necessary.

The height $h_2$ of the analyzer grating must be sufficient to produce effective absorption differences between the webs transirradiated by the X-radiation, and the largely free sites of the grating, in order to produce an appropriate Moiré pattern on the rear side.

For the purpose of better understanding, FIG. 3 once again shows—on the example of a situation with only a single analyzer grating $G_{11}$ being used—the individually coherent radiation that is coming from the grating $G_0$ and penetrates the patient P, phase shift phenomena coming about after the penetration of the patient P. As a result, when the grating $G_{11}$ is penetrated there is produced an interference pattern, illustrated by the gray shading, that, with the aid of the grating $G_2$ on the adjoining detector $D_1$ and the detector elements thereof, leads to different radiation intensities per detector element, a so-called Moiré pattern being formed there.

Figure 3:
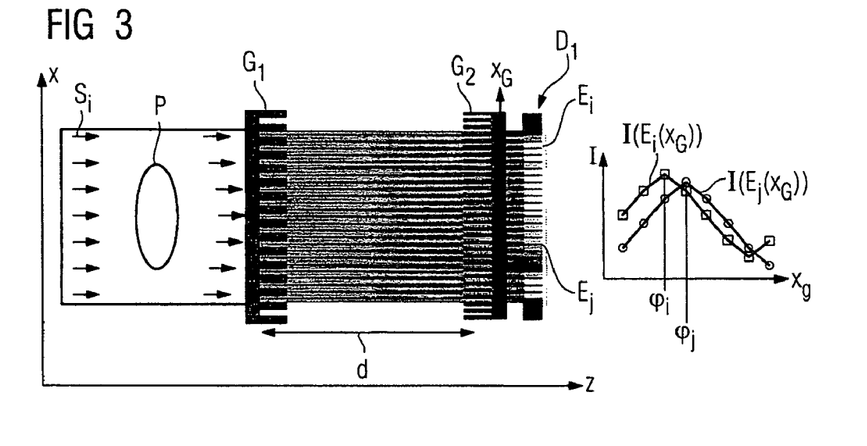
FIG. 3 shows a longitudinal section through a focus/detector system of a CT, including phase grating, analyzer grating and detector for displaying the interference phenomenon.

If, for example the detector element $E_i$ is considered as a function of an offset $x_G$ of the analyzer grating $G_2$, and if the intensity $I(E_i(x_G))$ is plotted as a function of the offset $x_G$ against the intensity I, the result is a sinusoidal rise and fall of the intensity I at this detector element $E_i$. If these measured radiation intensities I are plotted for each detector element $E_i$ or $E_j$ as a function of the offset $x_G$, the result for the various detector elements, which after all constitute the spatial X-ray beam between the focus and the respective detector element, is that the phase shift φ relative to one another can be determined for each detector element. It holds that:

$$\varphi = 2\pi n \frac{v}{\lambda},$$

v corresponding to the size of a voxel or pixel in the examined object, n being the refractive index thereof, and λ representing the wavelength of the X-radiation.

Thus, for each beam in space, it is possible by way of at least three measurements with an offset analyzer grating in each case to determine the phase shift per beam and for a narrow energy range of the radiation. If this is carried out likewise with the aid a further grating arrangement, which is tuned to another energy range, for each beam in space, a difference function $u(\phi(E1), \phi(E2))$ can be determined for each beam from knowledge of two different phase shifts $\phi(E1)$ and $\phi(E2)$) in conjunction with a different energy, from which either it is possible in the case of projective X-ray images to calculate pixel values of a projective image directly, or in the case of a CT examination projections are prepared whose pixel values correspond to the difference functions calculated in a beamwise fashion. It is possible therefrom with the aid of reconstruction methods known per se to calculate which volume element in the examination object is to be ascribed to which part of the measured difference functions.

It follows that what is calculated are either sectional images or volume data that reflect the spatial effect of the examined object on the difference functions. The function $$\frac{\varphi(E1) - \varphi(E2)}{\varphi(E1) + \varphi(E2)},$$

which constitutes a type of normalized energy-dependent phase shift gradient, can be used as preferred difference function. A corresponding statement is valid for the function $$\frac{n(E1) - n(E2)}{n(E1) + n(E2)},$$

which differs linearly merely in the conversion $$\varphi = 2\pi n \frac{v}{\lambda}$$

of the values.

Since even minor differences in the composition exert a strong effect on the energy dependence of the phase shift, very detailed and high-contrast volume data can be obtained thereby from materials that are relatively similar per se, in particular from soft tissue.

Instead of the above named difference functions, it is also possible for example, to form simple quotients or differences.

If the aim is now additionally also to prepare an absorption image by using the sum of the intensity measurements at the individual detector elements of a detector in order to determine the phase shift, it is possible by summing up the individual measurements for differently offset analyzer gratings to determine the effects of the analyzer grating therefrom, and thus to obtain a direct measure of the absorption values of the respective beam, that is to say it is possible on the basis of the measured data for the phase shift also to calculate a data record that reproduces an absorption value for each beam such that these absorption values can, in a way known per se, either be converted to direct projection absorption images or, with the aid of known reconstructions, be converted into tomographic absorption images. It is to be noted here that when use is made of the same energy spectrum for both measurements the energy dependence vanishes. If, however, different energy spectra are used, the energy dependence of the absorption can also be observed and, if appropriate, it is also possible to form corresponding difference functions and use them for the display.

Since the above described method for determining the phase shift of X-ray beams traversing an object is very energy-selective, the phase grating should be set with reference to its dimensions to energy ranges of the radiation used in which there is a photon number that is as high as possible.

Figure 4:
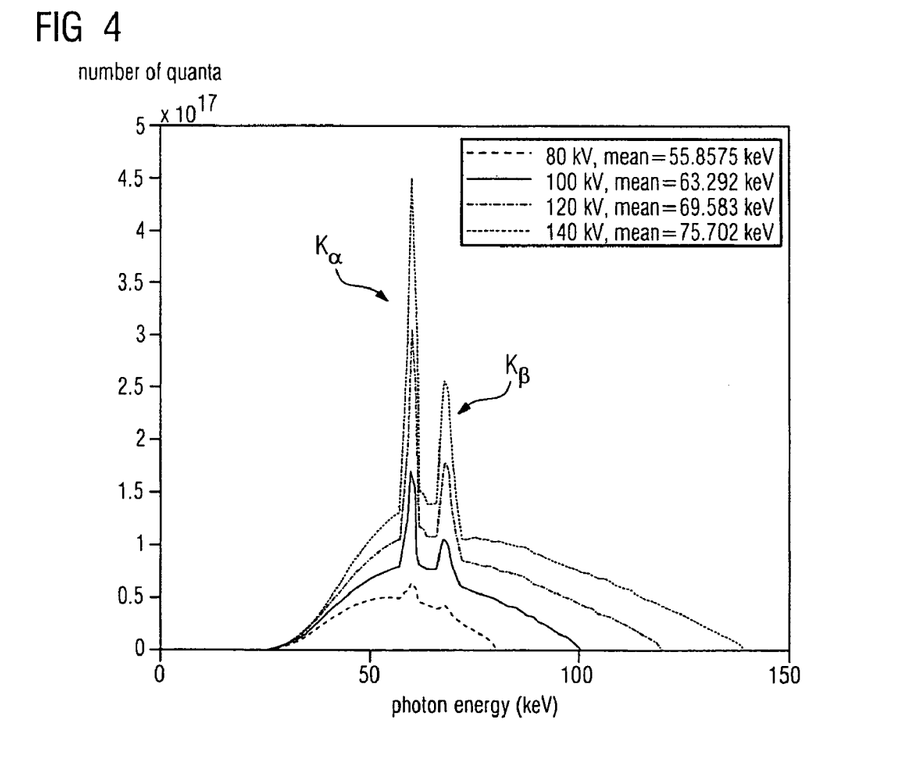
FIG. 4 shows the brems spectrum of a tungsten anode with characteristic lines for different acceleration voltages and the use of a hardening filter.

If, for example, a tungsten anode is being used, energy spectra result as a function of the acceleration voltage, as is illustrated in FIG. 4. Here, a strong respective peak is shown on the left and right in the energy spectra; it represents the characteristic radiation of the tungsten material used here. The $K_\alpha$ line is shown on the left, and the $K_\beta$ line on the right. It is particularly advantageous according to an embodiment of the invention when the phase gratings are oriented exactly with these characteristic lines with reference to their web height.

Figure 5:
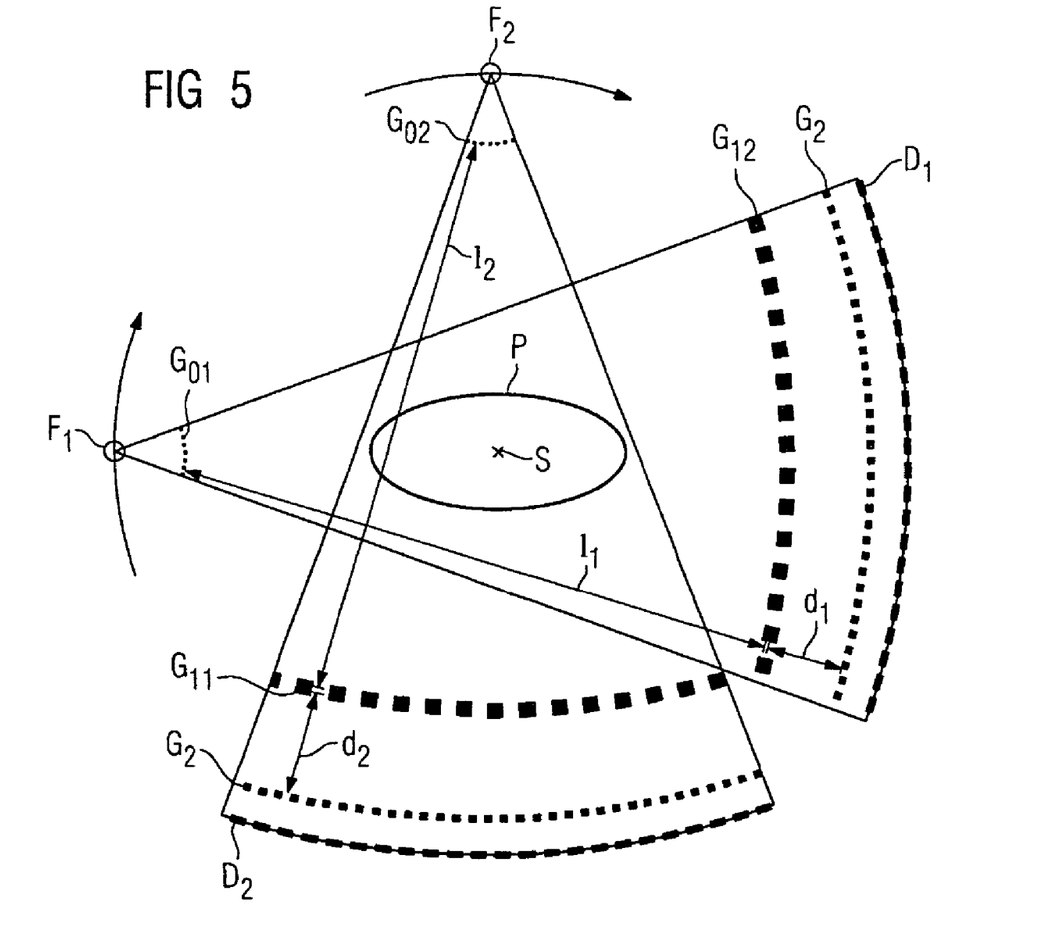
FIG. 5 shows a schematic sectional illustration of two focus/detector systems, offset by 90°, of a CT with different grating sets.

A further advantageous design of a CT system having two focus/detector systems $F_1$, $D_1$ and $F_2$, $D_2$ is shown in cross section schematically in FIG. 5. Both focus/detector systems are located on a common gantry and are correspondingly rotated at the same speed about the examination object, here a patient P, while the patient P is preferably displaced in the direction of the system axis S such that spiral scanning results. Respectively arranged in the two focus/detector systems $F_1$, $D_1$ and $F_2$, $D_2$ are different grating sets $G_{01}$, $G_{11}$, $G_2$ and $G_{02}$, $G_{12}$, $G_2$ that also exhibit different distances $d_1$, $l_1$ and $d_2$, $l_2$. Of course, the web heights of the phase gratings are also likewise adapted, correspondingly to the desired different radiation energy for which the phase shift is measured. It is possible in this way for the patient P to be scanned simultaneously with reference to different energy-dependent phase shifts, there being no restriction with reference to the use of different acceleration voltages in the two focus/detector systems $F_1$, $D_1$ and $F_2$, $D_2$.

Figure 6:
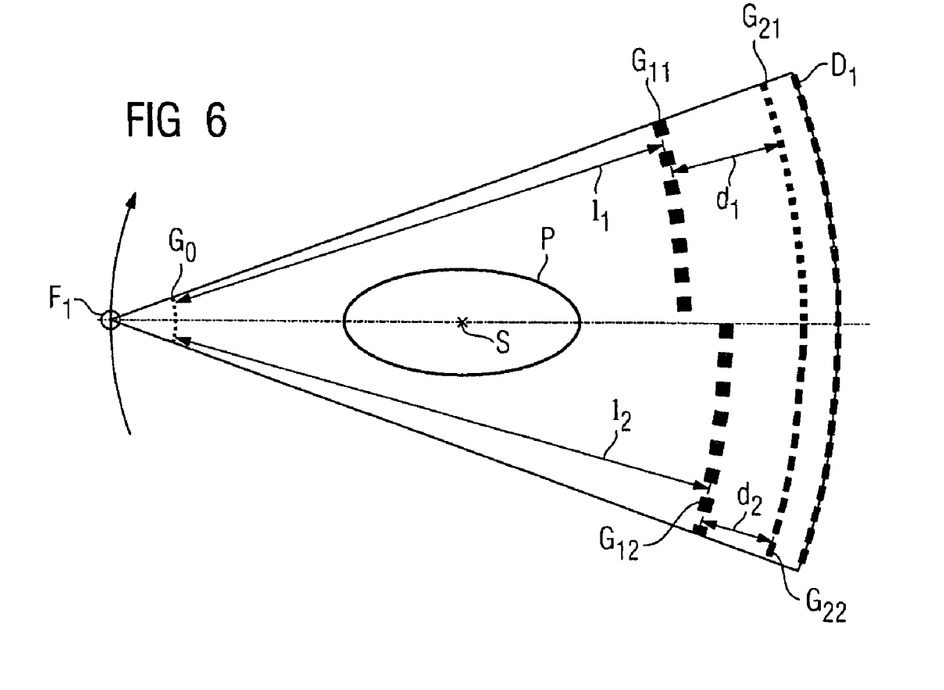
FIG. 6 shows a schematic sectional illustration of a split focus/detector system of a CT with different grating sets.

Another variant of the design of an embodiment of an inventive focus/detector system of a CT having a focus $F_1$ and a detector $D_1$ is shown in FIG. 6. Here, a single focus/detector system is equipped with two energy-specific grating arrangements $G_0$, $G_1$, $G_{21}$ and $G_0$, $G_{12}$, $G_{22}$, which also have different distances $d_1$, $l_1$ and $d_2$, $l_2$, each grating arrangement covering only a half of the fan angle of the focus/detector system. In this example, it is not the case that the source and phase gratings are different for the purpose of adapting to the different energy at which the phase shift is to be measured; rather, use is made of different phase and analyzer gratings, the source gratings being at the same distance from the analyzer grating but exhibiting a different period. A common source grating is used for the beam cone.

Figure 7:
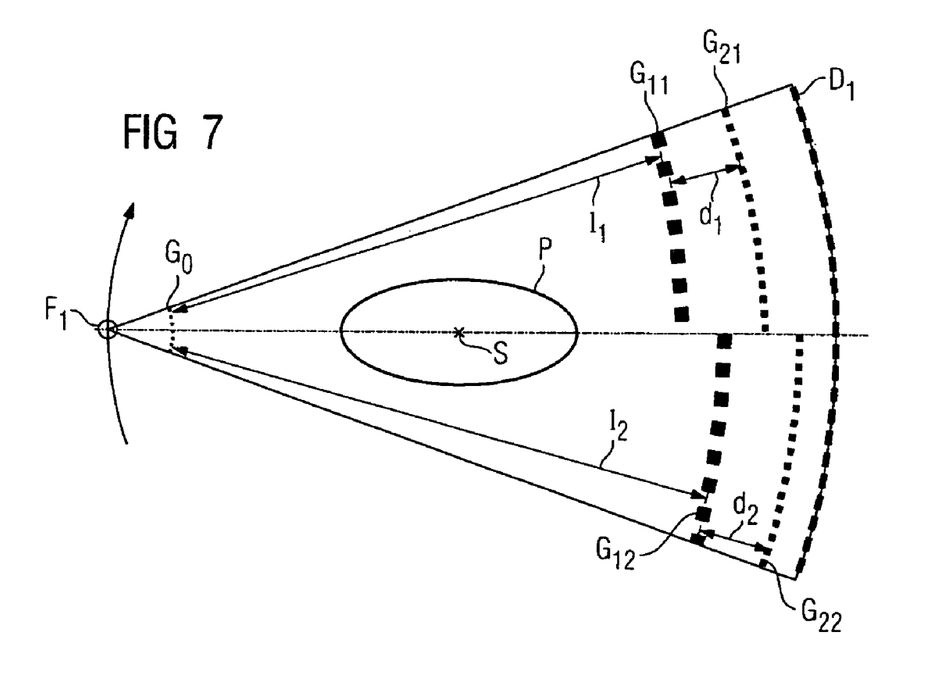
FIG. 7 shows a schematic sectional illustration of another split focus/detector system of a CT with different grating sets.

Another variant of the design of an embodiment of an inventive focus/detector system of a CT having a focus $F_1$ and a detector $D_1$ is shown in FIG. 7. Here, as well, a single focus/detector system is equipped with two energy-specific grating arrangements $G_0$, $G_{11}$, $G_{21}$ and $G_0$, $G_{12}$, $G_{22}$, which also have different distances each grating arrangement likewise covering only a half of the fan angle of the focus/detector system.

In this variant, different phase gratings are used in order to adapt to the different energy at which the phase shift is be measured, the two analyzer gratings being identical with reference to their period, but exhibiting different distances from the phase grating. Here, as well, the source grating remains the same. It could be advised by way of supplement in the case of this design likewise to divide the detector and arrange it at the shortest possible distance from the analyzer grating in each case.

It is true that the number of measurable projections is reduced to half in the variants of FIGS. 6 and 7 together with corresponding consequences for resolution and "signal-noise" ratio, but it is also possible in this way for a conventional CT having a single focus/detector system to simultaneously measure the phase shift at two different energies in a single pass, and exchanging the gratings is spared.

Figure 8:
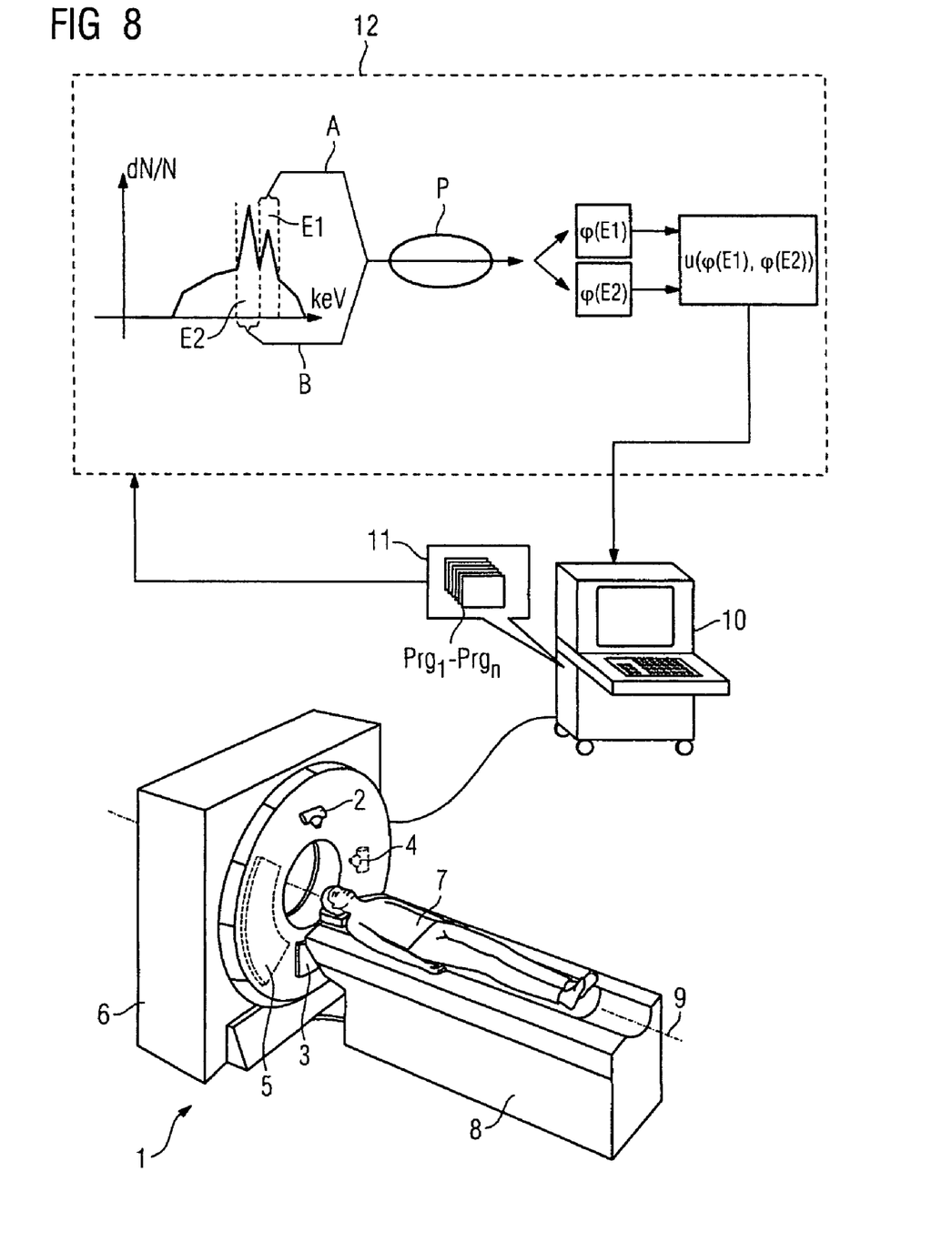
FIG. 8 shows a 3D illustration of an embodiment of an inventive CT system.

A complete computer CT system for carrying out an embodiment of the inventive method is demonstrated in FIG. 8. This shows the CT system 1, which has a first focus/detector system with an X-ray tube 2 and opposing detector 3, which are arranged on a gantry (not illustrated in greater detail) in a gantry housing 6. A grating system in accordance with FIGS. 1 to 3 is arranged in the beam path of the first focus/detector system 2, 3, such that the patient 7, who is located on a patient couch 8 that can be displaced along the system axis 9, can be pushed into the beam path of the first focus/detector system and scanned there. The control of the CT system is carried out by way an arithmetic and control unit 10 in which there are stored in a memory 11 programs $Prg_1$ to $Prg_n$ that carry out the previously described inventive methods, and reconstruct corresponding tomographic images from the measured radiation-dependent phase shifts and absorptions. The carrying out of these inventive methods is indicated in the box 12 illustrated with dashes.

Instead of the single focus/detector system, a second focus/detector system can optionally be arranged in the gantry housing. This is illustrated in FIG. 8 by the X-ray tube 4 shown with dashes, and by the detector 5 illustrated by dashes.

A schematic flow chart of the inventive method is shown in box 12. The energy spectrum, illustrated on the left, of a tungsten anode, which exhibits two characteristic X-ray lines, shows the energy spectrum used here. In a first path A, the phase contrast measurement is carried out by using this characteristic line and the large number of photons that occur there, while in the lower path B the same measurement is carried out, but in the region of the other characteristic radiation. As soon as the energy-specific phase shift φ(E1) and φ(E2) is determined for each beam through the patient P in the two energy ranges E1 and E2, the projections are calculated using the above described difference function u(φ(E1), φ(E2)), and fed to the reconstruction of tomographic images. In this way, tomographic images are produced with the aid of X-radiation and display very detailed structures even in zones of similar composition such as, for example, soft tissue.

It may be expressly pointed out that the technique described can also be applied in a simpler design to the preparation of projective images. When preparing projective images, it is possible to dispense with the rotating scanning of the examination objects, and with the reconstruction from protection data.

It remains to point out by way of supplement that not only is it possible to use the focus/detector system shown in order to measure phase shifts of the X-radiation, but that these also continue to be suitable for conventional measurement of the radiation absorption and reconstruction of corresponding absorption images. Appropriate, combined absorption and phase contrast images can also be produced.

It may be pointed out, furthermore, that the gaps between the grating lines can be filled with a highly absorbing material in the practical embodiment of the gratings used for the purpose of improving contrast. For example, gold may be used for this purpose. Fundamentally, at least the source and analyzer gratings functioning as absorption gratings should be configured such that they achieve a contrast factor of at least Overall, this document describes an embodiment of a method for producing projective and tomographic phase contrast images of an examination object, preferably a patient, having an X-ray system, and a corresponding X-ray system for carrying out this method, X-ray optical grating sets, tuned to different energy ranges, for determining energy-dependent phase shifts being used upon penetration of an examination object, a difference value being formed from these energy-dependent phase shifts, and tomographic or projective images being produced therefrom.

It goes without saying that the above named features of embodiments of the invention can be used not only in the combination respectively specified, but also in other combinations or on their own without departing from the scope of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing at least one of projective and tomographic images of an examination object using an X-ray system or X-ray CT system, comprising:

measuring a quantitative phase displacement of an X-radiation penetrating the examination object in an energy-specific fashion with reference to at least two different energy ranges; and forming recorded values as a function of the energy-specific quantitative phase displacements.

2. The method as claimed in claim 1, wherein the energy-specific quantitative phase displacements are determined for exactly two energy ranges.

3. The method as claimed in claim 1, wherein the value $$\frac{\varphi(E1) - \varphi(E2)}{\varphi(E1) + \varphi(E2)}$$

is used in the function of the energy-specific quantitative phase displacements (φ(E1), φ(E2)).

4. The method as claimed in claim 1, wherein the value $$\frac{\varphi(E1)}{\varphi(E2)}$$

is used in the function of the energy-specific quantitative phase displacements (φ(E1), φ(E2)).

5. The method as claimed in claim 1, wherein the value φ(E1)−φ(E2) is used in the function of the energy-specific quantitative phase displacements (φ(E1), φ(E2)).

6. The method as claimed in claim 1, wherein an energy-specific refractive index (n(E1), n(E2)) is calculated from the measured energy-specific quantitative phase displacements (φ(E1), φ(E2)), and is used for the recorded values.

7. The method as claimed in claim 6, wherein the energy-specific refractive indices (n(E1), n(E2)) are determined in accordance with the relationship $$\varphi = 2\pi n \frac{v}{\lambda},$$

representing the wavelength of the X-radiation of the energy range considered, and v representing the extent of a voxel.

8. The method as claimed in claim 7, wherein the value $$\frac{n(E1) - n(E2)}{n(E1) + n(E2)}$$

is used in the function of the energy-specific refractive indices (n(E1), n(E2)).

9. The method as claimed in claim 7, wherein the value $$\frac{n(E1)}{n(E2)}$$

is used in the function of the energy-specific refractive indices (n(E1), n(E2)).

10. The method as claimed in claim 7, wherein the value n(E1)−n(E2) is used in the function of the energy-specific refractive indices (n(E1), n(E2)).

11. The method as claimed in claim 1, wherein at least the following method steps are carded out in order to produce the tomographic X-ray phase contrast images:

the examination object is scanned with at least one focus/detector system in a circular or spiral fashion, the detector system having a multiplicity of juxtaposed detector elements that form at least one detector row, arranged between the at least one focus and the at least one detector for the purpose of measurement is a set of X-ray optical gratings that is transirradiated by the X-radiation, a field of radiation sources with individually coherent radiation being generated with the aid of at least one source grating between the focus and examination object, the examination object being penetrated by the X-radiation, and the X-radiation being subjected to a different quantitative phase quantitative displacement depending on the penetrated matter, an interference pattern of the radiation being generated with the aid of a first phase grating tuned to a first energy range, at least one further interference pattern of radiation being generated with the aid of at least one second phase grating tuned to another energy range, the radiation being guided to the detector through an analyzer grating, and the quantitative phase displacement of each beam upon passage through the examination object being determined by way of at least three intensity measurements of the same spatial beam with in each case a differently offset analyzer grating, and tomographic phase contrast data of the examination object are reconstructed from the measured quantitative phase displacements of the beams or refractive indices determined therefrom.

12. The method as claimed in claim 11, wherein a dedicated focus/detector system respectively having a grating set adapted in an energy-specific fashion is used for the measurements of the quantitative phase displacements per energy range, the focus/detector systems advantageously being arranged with an angular offset on a gantry.

13. The method as claimed in claim 11, wherein another phase grating in the same focus/detector system is used per energy range for the measurements of the quantitative phase displacements.

14. The method as claimed in claim 1, wherein the energy of a peak in the characteristic radiation of an anode material employed is used for at least one energy range to which at least one analyzer grating is tuned.

15. The method as claimed in claim 14, wherein the $K_\alpha$-line and $K_\beta$-line of the anode material is used for two energy ranges.

16. The method as claimed in claim 14, wherein the X-radiation for at least two different energy ranges is generated with the aid of different anode materials.

17. The method as claimed in claim 1, wherein at least the following method steps are carried out in order to produce the projective phase contrast images:

the examination object is transirradiated by a beam emanating from the focus of an X-ray tube, the received radiation intensity is measured with a detector, there being arranged between the at least one X-ray tube and the detector a set of X-ray optical gratings comprising at least one source grating, at least two different phase gratings alternately introduced into the beam path, and an analyzer grating, for each beam that lies in space between the focus and detector and penetrates the examination object, the quantitative phase displacement of this beam upon penetrating the object is determined by at least three intensity measurements with the aid of an analyzer grating arranged in each case with a different offset, and for each beam the pixel values are calculated as a function of the energy-specific quantitative phase displacements from the measured quantitative phase displacements for different energy ranges of each beam.

18. The method as claimed in claim 17, wherein the energy of a peak in the characteristic radiation of the anode material employed is used for at least one energy range to which at least one analyzer grating is tuned.

19. The method as claimed in claim 18, wherein the $K_\alpha$-line and $K_\beta$-line of the anode material is used for two energy ranges.

20. The method as claimed in claim 18, wherein the X-radiation for at least two different energy ranges is generated with the aid of different anode materials.

21. An X-ray CT system for producing tomographic phase contrast images, comprising:

at least one focus/detector system arranged on at least one of a gantry and a C arc to rotate about an examination object;

a set of transirradiated X-ray optical gratings between the focus and detector, including at least one source grating, at least two phase gratings alternately movable into the beam path, and an analyzer grating; and a control unit that contains program code for,
measuring a quantitative phase displacement of an X-radiation penetrating an examination object in an energy-specific fashion with reference to at least two different energy ranges, and
forming recorded values as a function of the energy-specific quantitative phase displacements.

22. An X-ray CT system for producing tomographic phase contrast images, comprising:

at least two focus/detector systems arranged on at least one of a gantry and a C arc to rotate about an examination object;

for each focus/detector system, a set of transirradiated X-ray optical gratings, dimensioned in an energy-specific fashion, between the focus and detector and including a source grating, a phase grating and an analyzer grating; and a control unit that contains program code for,
measuring a quantitative phase displacement of an X-radiation penetrating an examination object in an energy-specific fashion with reference to at least two different energy ranges, and
forming recorded values as a function of the energy-specific quantitative phase displacements.

23. The X-ray CT system as claimed in claim 21, further comprising:

an apparatus for relative displacement of the analyzer grating with reference to the phase grating in a fashion perpendicular to the beam direction and perpendicular to the longitudinal direction of the grating lines.

24. The X-ray CT system as claimed in claim 21, further comprising:

at least one further focus/detector system, arranged with an angular offset on the gantry, which is free from X-ray optical gratings and serves exclusively for absorption measurement.

25. The X-ray CT system as claimed in claim 21, wherein the grating arrangement satisfies the following geometric conditions:

for the first grating set:

$$p_{11} = 2 \times \frac{p_{01} \times p_2}{p_{01} + p_2}$$

$$p_{01} = p_2 \times \frac{l_1}{d_1},$$

$$d_1 = \frac{l_1 \times d_1^m}{l_1 - d_1^m} \text{ where } d_1^m = \frac{1}{2} \times \left(\frac{p_1^2}{4\lambda_1}\right),$$

$$h_{11} = \frac{\lambda_1}{2(n-1)},$$

and for the second grating set:

$$p_{12} = 2 \times \frac{p_{02} \times p_2}{p_{02} + p_2}$$

$$p_{02} = p_2 \times \frac{l_2}{d_2},$$

$$d_2 = \frac{l_2 \times d_2^m}{l_2 - d_2^m} \text{ where } d_2^m = \frac{1}{2} \times \left(\frac{p_2^2}{4\lambda_2}\right),$$

$$h_{12} = \frac{\lambda_2}{2(n-1)},$$

wherein:
$p_x$=Grating period of the grating $G_x$,
$p_{xy}$=Grating period of the grating $G_{xy}$,
$l_x$=Distance of the source grating $G_0$ from the phase grating $G_{1x}$ for the energy range $E_x$,
$d_x$=Distance of the phase grating $G_{1x}$ for the energy range $E_x$ from the analyzer grating $G_2$ in fan beam geometry,
$d_1$=Distance of the phase grating $G_{1x}$ for the energy range $E_x$ from the analyzer grating $G_2$ given parallel geometry,
$\lambda_x$=Wavelength of the radiation in the energy range $E_x$,
$h_{1x}$=Web height of the grating $G_{1x}$ for the energy range $E_x$ in the radiation direction, and
n=Refractive index of the grating material.

26. The X-ray CT system as claimed in claim 25, wherein the grating arrangement additionally satisfies the geometric condition $l_1+d_1=l_2+d_2$, and therefore $p_{01} \neq p_{02}$.

27. The X-ray CT system as claimed in claim 25, wherein the grating arrangement additionally satisfies the geometric condition $p_{01}=p_{02}$, and therefore $l_1+d_1 \neq l_2+d_2$.

28. The X-ray CT system as claimed in claim 25, wherein the grating arrangement satisfies both the geometric condition $p_{01} \neq p_{02}$, and the geometric condition $l_1+d_1 \neq l_2+d_2$.

29. An X-ray CT system for producing tomographic phase contrast images, comprising:
at least one focus/detector system arranged on at least one of a gantry and a C arc to rotate about an examination object;
a set of transirradiated X-ray optical gratings between the focus and detector, including at least one source grating, at least two phase gratings alternately movable into the beam path, and an analyzer grating; and
an arithmetic and control unit that contains program code fort
measuring a quantitative phase displacement of an X-radiation penetrating the examination object in an energy-specific fashion with reference to at least two different energy ranges, and
forming recorded values as a function of the energy-specific quantitative phase displacements.

30. A storage medium for a CT system, the storage medium including program code that, when executed, causes CT system to execute a method comprising:
measuring a quantitative phase displacement of an X-radiation penetrating an examination object in an energy-specific fashion with reference to at least two different energy ranges, and
forming recorded values as a function of the energy-specific quantitative phase displacements.

31. A focus/detector system of an X-ray apparatus, comprising:
a radiation source with a focus and an opposing planar detector with a multiplicity of detector elements;
a set of transirradiated X-ray optical gratings of parallel alignment, arranged between the focus and detector and by which a quantitative phase displacement in the radiation upon penetration of the examination object is measureable in a beamwise resolved fashion, the grating set including,
at least one source grating arranged between the at least one focus and the examination object,
at least two phase gratings arrangeable between the examination object and the detector and alternately introduceable into the beam path,
an analyzer grating arranged upstream of the detector, and
an apparatus for the relative displacement of the analyzer grating with reference to the phase gratings in a fashion perpendicular to the beam direction and perpendicular to the longitudinal direction of the grating lines; and
a control unit that contains program code for,
measuring the quantitative phase displacement of an X-radiation penetrating an examination object in an energy-specific fashion with reference to at least two different energy ranges, and
forming recorded values as a function of the energy-specific quantitative phase displacements.

32. An X-ray system comprising at least one focus/detector system as claimed in claim 31.

33. The X-ray system as claimed in claim 32, further comprising
means for calculating the phase shift from a number of intensity measurements of the same beam with the aid of a differently offset phase grating.

34. The X-ray system as claimed in claim 31, wherein the grating arrangement satisfies the following geometric conditions:
For the first grating set $$p_{11} = 2 \times \frac{p_{01} \times p_2}{p_{01} + p_2}$$

$$p_{01} = p_2 \times \frac{l_1}{d_1},$$

$$d_1 = \frac{l_1 \times d_1^m}{l_1 - d_1^m} \text{ where } d_1^m = \frac{1}{2} \times \left(\frac{p_1^2}{4\lambda_1}\right),$$

$$h_{11} = \frac{\lambda_1}{2(n-1)},$$

and for the second grating set:

$$p_{12} = 2 \times \frac{p_{02} \times p_2}{p_{02} + p_2}$$

$$p_{02} = p_2 \times \frac{l_2}{d_2},$$

$$d_2 = \frac{l_2 \times d_2^m}{l_2 - d_2^m} \text{ where } d_2^m = \frac{1}{2} \times \left(\frac{p_2^2}{4\lambda_2}\right),$$

$$h_{12} = \frac{\lambda_2}{2(n-1)},$$

wherein:
$p_x$=Grating period of the grating $G_x$,
$p_{xy}$=Grating period of the grating $G_{xy}$,
$l_x$=Distance of the source grating $G_0$ from the phase grating $G_{1x}$ for the energy range $E_x$,
$d_x$=Distance of the phase grating $G_{1x}$ for the energy range $E_x$ from the analyzer grating $G_2$ in fan beam geometry,
$d_1^=$=Distance of the phase grating $G_{1x}$ for the energy range $E_x$ from the analyzer grating $G_2$ given parallel geometry,
$\lambda_x$=Wavelength of the radiation in the energy range $E_x$,
$h_{1x}$=Web height of the grating $G_{1x}$ for the energy range $E_x$ in the radiation direction, and
n=Refractive index of the grating material.

35. The X-ray system as claimed in claim 34, wherein the grating arrangement additionally satisfies the geometric condition $l_1+d_1=l_2+d_2$, and therefore $p_{01} \neq p_{02}$.

36. The X-ray system as claimed in claim 34, wherein the grating arrangement additionally satisfies the geometric condition $P_{01}=p_{02}$, and therefore $l_1+d_1 \neq l_2+d_2$.

37. The X-ray system as claimed in claim 34, wherein the grating arrangement satisfies both the geometric condition $p_{01} \neq p_{02}$, and the geometric condition $l_1+d_1 \neq l_2+d_2$.

38. A focus/detector system of an X-ray apparatus, comprising:
a radiation source with a focus and an opposing planar detector with a multiplicity of detector elements;
a set of transirradiated X-ray optical gratings of parallel alignment, arranged between the focus and detector and by which a quantitative phase displacement in the radiation upon penetration of the examination object is measureable in a beamwise resolved fashion, the grating set including
at least one source grating arranged between the at least one focus and the examination object,
at least two phase gratings arrangeable between the examination object and the detector and alternately introduceable into the beam path,
an analyzer grating arranged upstream of the detector, and
an apparatus for the relative displacement of the analyzer grating with reference to the phase gratings in a fashion perpendicular to the beam direction and perpendicular to the longitudinal direction of the grating lines; and
an arithmetic and control unit that contains program code for execution of,
measuring the quantitative phase displacement of an X-radiation penetrating the examination object in an energy-specific fashion with reference to at least two different energy ranges, and
forming recorded values as a function of the energy-specific quantitative phase displacements.

39. A storage medium for an X-ray system, wherein the storage medium contains program code that, when executed, causes X-ray system to perform a method comprising:
measuring a quantitative phase displacement of an X-radiation penetrating an examination object in an energy-specific fashion with reference to at least two different energy ranges, and
forming recorded values as a function of the energy-specific quantitative phase displacements.

40. The method as claimed in claim 2, wherein the value $$\frac{\varphi(E1) - \varphi(E2)}{\varphi(E1) + \varphi(E2)}$$

is used in the function of the energy-specific quantitative phase displacements ($\phi(E1)$, $\phi(E2)$).

41. The method as claimed in claim 2, wherein the value $$\frac{\varphi(E1)}{\varphi(E2)}$$

is used in the function of the energy-specific quantitative phase displacements ($\phi(E1)$, $\phi(E2)$).

42. The method as claimed in claim 2, wherein the value $\phi(E1)-\phi(E2)$ is used in the function of the energy-specific quantitative phase displacements ($\phi(E1)$, $\phi(E2)$).

43. The method as claimed in claim 2, wherein an energy-specific refractive index (n(E1), n(E2)) is calculated from the measured energy-specific quantitative phase displacements ($\phi(E1)$, $\phi(E2)$), and is used for the recorded values.

44. The X-ray CT system as claimed in claim 22, further comprising:
an apparatus for relative displacement of the analyzer grating with reference to the phase grating in a fashion perpendicular to the beam direction and perpendicular to the longitudinal direction of the grating lines.

45. The X-ray CT system as claimed in claim 22, further comprising:
at least one further focus/detector system, arranged with an angular offset on the gantry, which is free from X-ray optical gratings and serves exclusively for absorption measurement.

46. The X-ray CT system as claimed in claim 22, wherein the grating arrangement satisfies the following geometric conditions:
for the first grating set:

$$p_{11} = 2 \times \frac{p_{01} \times p_2}{p_{01} + p_2}$$

$$p_{01} = p_2 \times \frac{l_1}{d_1},$$

$$d_1 = \frac{l_1 \times d_1^=}{l_1 - d_1^=} \text{ where } d_1^= = \frac{1}{2} \times \left(\frac{p_1^2}{4\lambda_1}\right),$$

$$h_{11} = \frac{\lambda_1}{2(n-1)},$$

and for the second grating set:

$$p_{12} = 2 \times \frac{p_{02} \times p_2}{p_{02} + p_2}$$

$$p_{02} = p_2 \times \frac{l_2}{d_2},$$

$$d_2 = \frac{l_2 \times d_2^=}{l_2 - d_2^=} \text{ where } d_2^= = \frac{1}{2} \times \left(\frac{p_2^2}{4\lambda_2}\right),$$

$$h_{12} = \frac{\lambda_2}{2(n-1)},$$

wherein:
$P_x$=Grating period of the grating $G_x$,
$p_{xy}$=Grating period of the grating $G_{xy}$,
$l_x$=Distance of the source grating $G_0$ from the phase grating $G_{1x}$ for the energy range $E_x$,
$d_x$=Distance of the phase grating $G_{1x}$ for the energy range $E_x$ from the analyzer grating $G_2$ in fan beam geometry,
$d_1^=$=Distance of the phase grating $G_{1x}$ for the energy range $E_x$ from the analyzer grating $G_2$ given parallel geometry,
$\lambda_x$=Wavelength of the radiation in the energy range $E_x$,
$h_{1x}$=Web height of the grating $G_{1x}$ for the energy range $E_x$ in the radiation direction, and
n=Refractive index of the grating material.

47. A focus/detector system of an X-ray apparatus, comprising:
a radiation source with a focus and an opposing planar detector with a multiplicity of detector elements;
a set of transirradiated X-ray optical gratings of parallel alignment, arranged between the focus and detector and by which the phase shift in the radiation upon penetration of the examination object is measureable in a beamwise resolved fashion, the grating set including
at least one source grating arranged between the at least one focus and the examination object,
at least two phase gratings arrangeable between the examination object and the detector and alternately introduceable into the beam path,
an analyzer grating arranged upstream of the detector, and
an apparatus for the relative displacement of the analyzer grating with reference to the phase gratings in a fashion perpendicular to the beam direction and perpendicular to the longitudinal direction of the grating lines; and
an arithmetic and control unit that contains program code for exeei44 on measuring a phase shift of an X-radiation penetrating the examination object in an energy-specific fashion with reference to at least two different energy ranges, and
forming recorded values as a function of the energy-specific phase shifts, wherein in order to produce the projective phase contrast images,
the examination object is transirradiated by a beam emanating from the focus of an X-ray tube,
the received radiation intensity is measured with a detector, there being arranged between the at least one X-ray tube and the detector a set of X-ray optical gratings comprising at least one source grating, at least two different phase gratings alternately introduced into the beam path, and an analyzer grating,
for each beam that lies in space between the focus and detector and penetrates the examination object, the phase shift of this beam upon penetrating the object is determined by at least three intensity measurements with the aid of an analyzer grating arranged in each case with a different offset, and
for each beam the pixel values are calculated as a function of the energy-specific phase shifts from the measured phase shifts for different energy ranges of each beam.

48. A storage medium for an X-ray system, wherein the storage medium contains program code that, when executed, causes the X-ray system to perform a method comprising:
measuring a phase shift of an X-radiation penetrating the examination object in an energy-specific fashion with reference to at least two different energy ranges, and
forming recorded values as a function of the energy-specific phase shifts, wherein in order to produce the projective phase contrast images,
the examination object is transirradiated by a beam emanating from the focus of an X-ray tube,
the received radiation intensity is measured with a detector, there being arranged between the at least one X-ray tube and the detector a set of X-ray optical gratings comprising at least one source grating, at least two different phase gratings alternately introduced into the beam path, and an analyzer grating,
for each beam that lies in space between the focus and detector and penetrates the examination object, the phase shift of this beam upon penetrating the object is determined by at least three intensity measurements with the aid of an analyzer grating arranged in each case with a different offset, and
for each beam the pixel values are calculated as a function of the energy-specific phase shifts from the measured phase shifts for different energy ranges of each beam.

49. An X-ray CT system for producing tomographic phase contrast images, comprising:
at least one focus/detector system arranged on at least one of a gantry and a C arc to rotate about an examination object;
a set of transirradiated X-ray optical gratings between the focus and detector, including at least one source grating, at least two phase gratings alternately movable into the beam path, and an analyzer grating; and
at least one further focus/detector system, arranged with an angular offset on the at least one of the gantry and the c arc, which is free from X-ray optical gratings and serves exclusively for absorption measurement.

* * * * *